US00PP36908P2

(12) United States Plant Patent
Bacon et al.

(10) Patent No.: US PP36,908 P2
(45) Date of Patent: Sep. 2, 2025

(54) GRAPEVINE PLANT NAMED 'SUGRA71'

(50) Latin Name: *Vitis vinifera*
Varietal Denomination: SUGRA71

(71) Applicant: Sun World International, LLC, Wasco, CA (US)

(72) Inventors: Terry A. Bacon, Maplewood, NJ (US); Terrence J Frett, Bakersfield, CA (US)

(73) Assignee: Sun World International, LLC, Wasco, CA (US)

( * ) Notice: Subject to any disclaimer, the term of this patent is extended or adjusted under 35 U.S.C. 154(b) by 0 days.

(21) Appl. No.: 19/065,170

(22) Filed: Feb. 27, 2025

(51) Int. Cl.
*A01H 5/08* (2018.01)
*A01H 6/88* (2018.01)

(52) U.S. Cl.
USPC ..... Plt./205
CPC ..... *A01H 6/88* (2018.05); *A01H 5/08* (2013.01)

(58) Field of Classification Search
USPC ..... Plt./205, 206
See application file for complete search history.

(56) References Cited

U.S. PATENT DOCUMENTS

PP21,664 P3 * 1/2011 Cain ..... A01H 6/88 Plt./308

* cited by examiner

*Primary Examiner* — Susan McCormick Ewoldt
(74) *Attorney, Agent, or Firm* — Knobbe, Martens, Olson & Bear, LLP

(57) ABSTRACT

The new variety of grapevine 'SUGRA71' is characterized by the production of a large-sized, dark red and obtuse ovate berry with a very late season ripening date. The berries of 'SUGRA71' are moderately firm and very juicy.

1 Drawing Sheet

Latin name of the genus and species claimed: *Vitis vinifera.*

Variety denomination: 'SUGRA71'.

BACKGROUND AND SUMMARY

This application relates to the discovery and asexual propagation of a new and distinct variety of grapevine 'SUGRA71', as herein described and illustrated. The new variety was first selected as breeder number 'GR1109R' by Terry A. Bacon and Terrence J. Frett in Wasco, Kern County, California in July 2021. The variety was originated by controlled hybridization.

The new variety 'SUGRA71' is characterized by the production of a large-sized, dark red and obtuse ovate berry with a very late season ripening date. The berries of 'SUGRA71' are moderately firm and very juicy.

The seed parent is 'Sugrafortyeight' (U.S. Plant Pat. No. 27,791) and the pollen parent is 'Sugra60' (U.S. Plant Pat. No. 34,697). The parent varieties were first crossed in April 2019. The date of first sowing was March 2020, and the date of first flowering was April 2021.

The new variety 'SUGRA71' was first asexually propagated in December 2021 in Wasco, Kern County, California, by Terry A. Bacon and Terrence J. Frett using hardwood cuttings.

The new variety 'SUGRA71' can be distinguished from its pollen parent 'SUGRA60' (U.S. Plant Pat. No. 34,697) in that while both varieties have dark red colored and obtuse ovate shaped berries, ripening of the berries of the new variety 'SUGRA71' starts on September 25$^{th}$ compared to July 22$^{d}$ for 'SUGRA60'. Additionally, the new variety 'SUGRA71' has a lower berry weight at 9 g, compared to 9.5 g for 'SUGRA60'.

The new variety 'SUGRA71' is distinguished from its seed parent 'Sugrafortyeight' (U.S. Plant Pat. No. 27,791) in that while both varieties have rudimentary seed traces, the new variety 'SUGRA71' has dark red berries compared to black colored berries for 'Sugrafortyeight'. Additionally, the new variety 'SUGRA71' has an obtuse ovate berry shape with a berry weight of 9 g compared to the broad elliptic berry shape and berry weight of 11.8 g for 'Sugrafortyeight'. Further, the new variety 'SUGRA71' has a cluster weight of 750 g compared to 870 g for 'Sugrafortyeight'.

The fruit of the new variety 'SUGRA71' has rudimentary seed traces like 'IFG-68-175' (U.S. Plant Pat. No. 21,664), but the new variety 'SUGRA71' has an obtuse ovate shaped berry, compared to a broad elliptic shape for the berries of 'IFG-68-175'. Further, SUGRA71' has a berry weight of 9 g, compared to 7.5 g for the berries of 'IFG-68-175'.

The fruit of the new variety 'SUGRA71' has rudimentary seed traces like 'Crimson Seedless' (Unpatented), but the new variety 'SUGRA71' has a berry weight of 9 g and cluster weight of 750 g, compared to a berry weight of 6.2 g and a cluster weight of 600 g for 'Crimson Seedless'. Further, the ripening of the berries of the new variety 'SUGRA71' starts on September 25$^{th}$, compared to September 8$^{th}$ for 'Crimson Seedless'.

The fruit of the new variety 'SUGRA71' has rudimentary seed traces like 'Sheegene-13' (U.S. Plant Pat. No. 20, 110), but the new variety 'SUGRA71' has a berry weight of 9 g and cluster weight of 750 g, compared to a berry weight of 8 g and cluster weight of 600 g for 'Sheegene-13'. Additionally, the new variety 'SUGRA71' has an obtuse ovate shaped berry, compared to an ovate shaped berry for 'Sheegene-13'.

The new 'SUGRA71' variety has been shown to maintain its distinguishing characteristics through successive asexual propagations by, for example, cuttings and grafting.

Variations of the usual magnitude from the characteristics described herein may occur with changes in any of a variety of factors such as growing conditions, irrigation, fertilization, pruning, management and climatic variation.

BRIEF DESCRIPTION OF THE DRAWING

The accompanying color photographic illustration taken from a 3-year-old plant shows typical specimens of the foliage and fruit of the new grape variety 'SUGRA71'.

The illustration shows the upper and lower surfaces of the leaves and exterior and sectional views of the fruit.

The photographic illustration was taken shortly after the fruit was picked and the colors are as nearly true as is reasonably possible in a color representation of this type.

DETAILED DESCRIPTION

Throughout this specification, color names beginning with a small letter signify that the name of that color, as used in common speech, is aptly descriptive. Color names beginning with a capital letter designate values based upon the R.H.S. Colour Chart, published by The Royal Horticultural Society, London, England, sixth edition, 2019 reprint.

Many of the descriptive values in this specification are based on and conform to those set forth by the International Board for Plant Genetic Resources Institute Grape Descriptors (*Vitis* spp.) of 1983 and/or 1997, which was developed in collaboration with the Office International de la Vigne et du Vin (OIV) and the International Union for the Protection of New Varieties of Plants (UPOV).

The descriptive matter which follows pertains to four-year-old 'SUGRA71' plants grown in the vicinity of Wasco, Kern County, California during 2024, and is believed to apply to plants of the variety grown under similar conditions of soil and climate elsewhere.

VINE

General: (Measurements taken on three-year-old plant).

- *Vine size*.—Large. Height: Approximately 2.0 m. Width: Approximately 2.5 m.
- *Vigor*.—Vigorous.
- *Density of foliage*.—Dense.
- *Productivity*.—Very productive.
- *Crop load*.—Approximately 30 kg per vine after thinning.
- *Own root*.—Yes.
- *Training method*.—Typically cane pruned leaving about 6 canes.
- *Resistance*.—Neither resistance nor susceptibility to particular diseases or pests has been observed in this variety.

Trunk:

- *Shape*.—Stocky.
- *Diameter*.—Approximately 5 cm (at 30 cm above the soil line).
- *Straps*.—Long.
- *Surface texture*.—Medium shaggy.
- *Inner and outer bark color*.—Inner bark about Medium Greyed-Orange 166C, weathering to about Dark Greyed-Green 197B in the outer bark.

SHOOTS

Young shoot:

- *Form of tip*.—Wide open.
- *Intensity of anthocyanin coloration of tip*.—Medium.
- *Density of prostrate hairs on tip*.—Medium.
- *Density of erect hairs on tip*.—Medium.
- *Color*.—About Medium Green 143A.
- *Vigor during flowering*.—Strong.

Woody shoot (observations made in the middle third of shoot):

- *Attitude before tying*.—Semi-drooping.
- *Growth of axillary shoots*.—Medium, about 16 cm in length.
- *Internode length*.—Very short, approximately 55 mm.
- *Width at node*.—Approximately 10 mm.
- *Cross section*.—Circular.
- *Surface texture*.—Striated.
- *Main color*.—About Medium Greyed-Orange 166C.
- *Color of dorsal side of internode*.—About Medium Greyed-Orange 166C.
- *Color of ventral side of internode*.—About Medium Greyed-Orange 166C.
- *Color of dorsal side of node*.—About Medium Greyed-Orange 166C and Dark Greyed-Orange 166A.
- *Color of ventral side of node*.—About Medium Greyed-Orange 166C and Dark Greyed-Orange 166A.
- *Density of erect hairs on nodes*.—Absent.
- *Density of erect hairs on internodes*.—Absent or Very Sparse.
- *Density of prostrate hairs on internodes*.—Absent or Very Sparse.
- *Density of prostrate hairs on nodes*.—Absent or Very Sparse.

Tendrils:

- *Distribution on the shoot at full flowering*.—Discontinuous.
- *Thickness*.—Approximately 1 mm.
- *Color*.—About Light Green 141D in mid-summer.
- *Form*.—Bifurcated.
- *Number of consecutive tendrils*.—About 2.
- *Length of tendril*.—Short, approximately 13 cm.

LEAVES

Young leaves:

- *Color of upper surface of first* 4 *distal unfolded leaves*.—About Dark Yellow-Green 147A.
- *Average intensity of anthocyanin coloration of six distal leaves prior to flowering*.—Present, about 80% of the leaf blade is a mixture of green and light copper red.
- *Density of prostrate hairs between veins at lower surface of* 4*th distal unfolded leaf*.—Absent or very sparse.
- *Density of erect hairs between veins at lower surface of* 4*th distal unfolded leaf*.—Absent or very sparse.
- *Density of prostrate hairs on veins at lower surface of* 4*th distal unfolded leaf*.—Absent or very sparse.
- *Density of erect hairs on veins at lower surface of* 4*th distal unfolded leaf*.—Absent or very sparse.

Mature leaves (observations made on leaves in the middle third of shoot):

*Size*.—Large.

*Average length*.—Approximately 17 cm without petiole.

*Average width*.—Approximately 12 cm.

*Shape of blade*.—Wedge-shaped.

*Number of lobes*.—Approximately 5.

*Mature leaf profile*.—Undulate.

*Blistering surface of blade upper surface*.—Absent or very weak.

*Goffering of blade*.—Absent or very weak.

*Leaf blade tip*.—In the plane of the leaf.

*Undulation of margin*.—Slightly undulating.

*Undulation of blade between main and lateral veins*.—Overall.

*Thickness*.—Average-typical of *Vitis vinifera* species.

*Overall shape of teeth*.—Mixture of both sides straight and both sides convex.

*Length of teeth*.—Medium, ranging from about 3 mm to 12 mm.

*Ratio length/width of teeth*.—Small, nearly 1:1.

*General shape of petiole sinus lobes*.—Wide open.

*Shape of base of petiole sinus*.—U-shaped.

*Tooth at petiole sinus*.—Absent.

*Petiole sinus limited by veins*.—Absent.

*Shape of upper leaf sinuses*.—U-shaped.

*Shape of upper lateral sinus lobes*.—Slightly overlapping.

*Depth of upper lateral sinuses*.—Deep, approximately 4 cm to 5 cm.

*Density of prostrate hairs between veins on lower surface of blade*.—Absent to very sparse.

*Density of erect hairs between veins on lower surface of blade*.—Absent to very sparse.

*Density of prostrate hairs on main veins on lower surface of blade*.—Absent to very sparse.

*Density of erect hairs on main veins on lower surface of blade*.—Absent to very sparse.

*Density of prostrate hairs on main veins on upper surface of blade*.—Absent to very sparse.

*Autumn coloration of leaves*.—Usually about Light Green 138B becoming about Medium Grey-Brown 199C.

Upper leaf surface:

*Color*.—About Dark Green 139A.

*Surface texture*.—Smooth.

*Surface appearance*.—Dull.

*Upper surface anthocyanin coloration of main veins*.—Low.

Lower leaf surface:

*Color*.—About Light Green 139B.

*Surface texture*.—Smooth.

*Surface appearance*.—Dull.

*Anthocyanin coloration of main veins*.—Low.

Petiole:

*Length of petiole*.—Approximately 10 cm.

*Diameter*.—Approximately 3 mm.

*Length of petiole compared to middle vein*.—Slightly shorter; about 10 cm for the petiole compared to 13 cm for middle vein.

*Density of prostrate hairs on petiole*.—Absent.

*Density of erect hairs on petiole*.—Absent.

*Color*.—About Medium Yellow-Green 147B with tones of Medium Greyed-Red 182B.

Buds:

*Shape*.—Conical.

*Size*.—Medium, approximately 3 mm wide x 4 mm long.

*Position*.—Slightly held out.

*Bud fruitfulness*.—Basal, mostly fruitful.

*Time of bud burst*.—Medium, approximately March 18th for the southern San Joaquin Valley region of California.

*Anthocyanin coloration of buds*.—Weak.

FLOWERS

General:

*Flower type*.—Fully developed stamen and fully developed gynoecium.

*Position of first flowering node*.—Usually 3$^{rd}$ node of current season growth.

*Number of inflorescences per shoot*.—Averages 2.

*Time of full bloom*.—Approximately May 6 in the southern San Joaquin Valley region of California.

FRUIT

General:

*Ripening period*.—Very late season, beginning about September 25th in the southern San Joaquin Valley region of California.

*Use*.—Fresh market.

*Storage quality*.—Good.

Cluster:

*Form*.—Short conical.

*Cluster size* (*peduncle excluded*).—Large.

*Cluster length* (*peduncle excluded*).—Approximately 17 cm.

*Cluster width*.—Approximately 17 cm.

*Cluster weight*.—Approximately 750 g.

*Cluster density*.—Loose.

*Number of berries*.—Approximately 90 berries after tipping.

Peduncle:

*Length*.—Medium, approximately 5 cm.

*Diameter*.—Approximately 5 mm.

*Lignification of peduncle*.—Medium.

*Color*.—About Medium Greyed-Purple 184B.

Berry:

*Size*.—Large, approximate weight 9 g.

*Dimensions*.—Width: Approximately 22 mm. Length: Approximately 25 mm.

*Uniformity of size*.—Somewhat uniform.

*Shape*.—Obtuse ovate.

*Cross section*.—Circular.

*Skin color* (*without bloom*).—About Medium Red-Purple 70A.

*Flesh color*.—About Medium Green N138C.

*Anthocyanin color of flesh*.—Absent or very weak.

*Bloom* (*cuticular wax*).—Medium, typical of most commercial *Vitis vinifera*.

*Pedicel length*.—Approximately 10 mm.

*Pedicel thickness*.—Medium, approximately 1.9 mm.

*Berry separation from pedicel*.—Moderately easy.

*Seed traces*.—Rudimentary.

*Berry firmness*.—Moderately firm.

*Flesh juiciness*.—Very juicy.

*Flesh texture*.—Firm and meaty.

*Particular flavor*.—Fruity.

*Refractometer test*.—About 18 Brix.

*Titratable acidity*.—About 0.40%.

*Brix:acid ratio*.—Approximately 45.

Skin:

*Skin thickness*.—Medium, about 175 um.

*Skin texture*.—Smooth.

*Skin reticulation*.—Absent.

*Skin tenacity*.—Tenacious to flesh.

*Skin tendency to crack*.—Rare.

*Skin sensitivity to sunburn*.—None.

What is claimed is:

1. A new and distinct variety of grapevine 'SUGRA71' as herein illustrated and described.

* * * * *

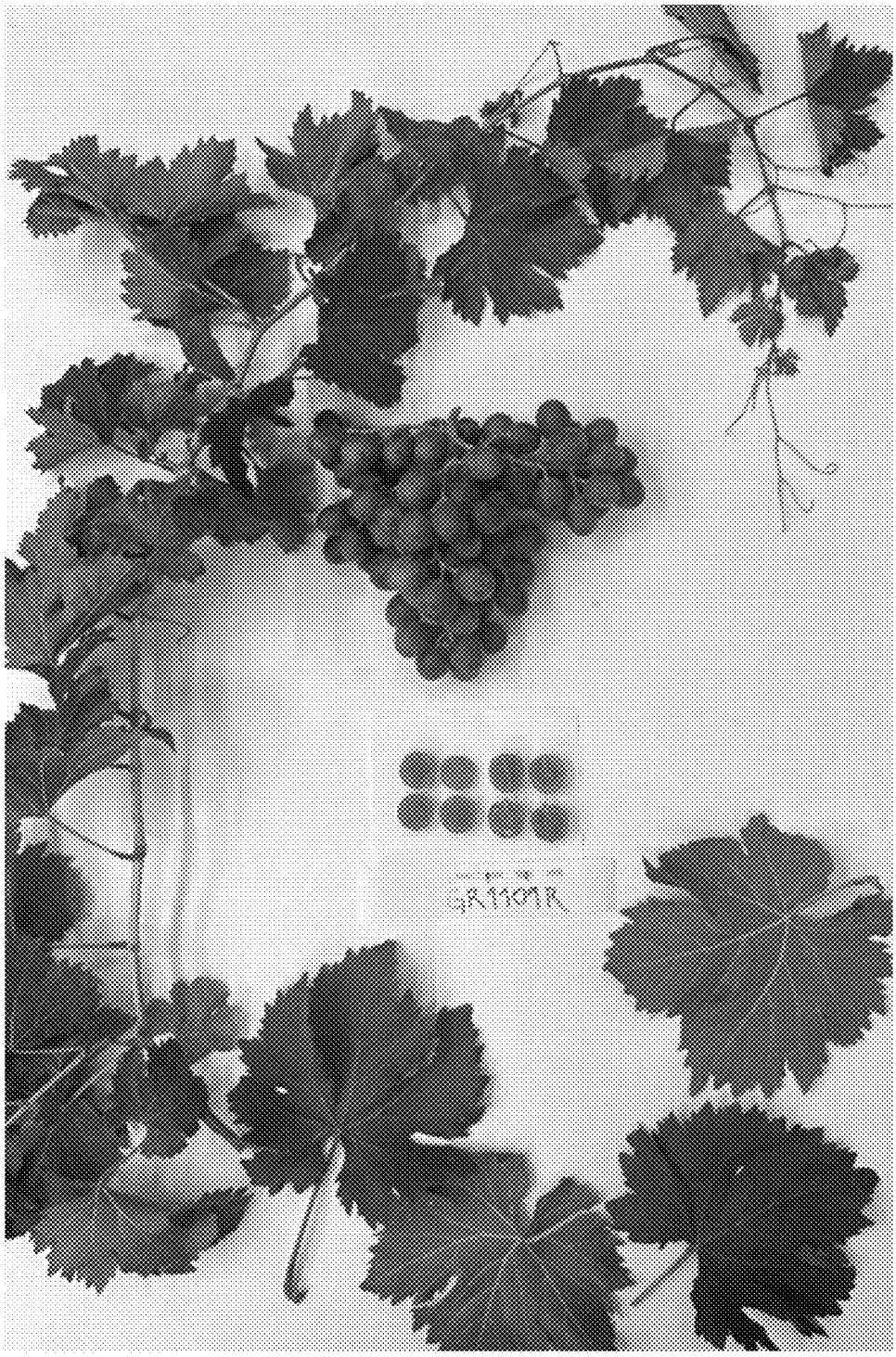
GRIMOR